United States Patent [19]

Girault

[11] Patent Number: 5,686,829
[45] Date of Patent: Nov. 11, 1997

[54] VOLTAMMETRIC METHOD AND APPARATUS

[75] Inventor: Hubert Girault, Ropraz, Switzerland

[73] Assignee: Metrohm AG, Herisau, Switzerland

[21] Appl. No.: 444,011

[22] Filed: May 18, 1995

[30] Foreign Application Priority Data

Jun. 3, 1994 [CH] Switzerland ............................. 1752/94

[51] Int. Cl.[6] .................................................. G01N 27/26
[52] U.S. Cl. ........................... 324/72; 324/447; 324/450; 204/412; 204/415
[58] Field of Search ............................ 204/400, 412, 204/415, 434; 324/72, 439, 450, 444–449

[56] References Cited

U.S. PATENT DOCUMENTS

| 4,584,530 | 4/1986 | Nicholson | 324/450 |
| 5,074,977 | 12/1991 | Cheung et al. | 204/400 |
| 5,092,980 | 3/1992 | Maurer et al. | 204/415 |
| 5,108,564 | 4/1992 | Szuminsky et al. | 204/412 |
| 5,200,706 | 4/1993 | Yada | 324/450 |
| 5,217,112 | 6/1993 | Almon | 204/412 |
| 5,395,504 | 3/1995 | Sauer et al. | 204/412 |
| 5,470,484 | 11/1995 | McNeel | 324/439 X |

FOREIGN PATENT DOCUMENTS

| 59-030055 | 2/1984 | Japan | 324/450 |
| 4-344452 | 12/1992 | Japan | 324/450 |
| 5-256810 | 10/1993 | Japan | 324/450 |
| WO91/08474 | 6/1991 | WIPO . | |

*Primary Examiner*—Ernest F. Karlsen
*Assistant Examiner*—Diep Do

[57] ABSTRACT

During voltammetric analysis of liquids, the indicator electrode must be frequently changed in order to prevent memory effects and resultant changes to basic conditions during measurement. In order to be able to change the indicator electrodes simply, a plurality of indicator electrodes are arranged on a common carrier. For accommodation of the liquid (2) to be analysed, a vessel (1) is provided and the carrier (5) is mounted to move in relation to this vessel (1) in such a way that one of the indicator electrodes (6) can be selectively brought into the area intended for the liquid. The reference electrode (8) necessary for the measurement is arranged in the vessel (1) and likewise connected with the measuring device (20). With that, changing of the selected electrode (6) ensues by moving the carrier (5) relative to said vessel (1).

17 Claims, 5 Drawing Sheets

VOLTAMMETRIC METHOD AND APPARATUS

The invention concerns a device for voltammetry according to the preamble of claim 1, an arrangement of indicator electrodes for such a device, in particular as part of a tape cassette, as well as a method of carrying out voltammetric analysis according to the preamble to claim 17.

BACKGROUND OF THE INVENTION

Voltammetry is an electrochemical method for the analysis substances, with which current voltage curves are measured and evaluated. A reference electrode and an indicator electrode are immersed into the liquid to be analysed. These are connected to an electrical measuring device with which a known potential drop between reference electrode and indicator electrode can be generated. In voltammetry, this potential is changed in a specific way, and information about the liquid to be analysed can be gained from the resultant current change. In modern polarography, the three-electrode principle is almost exclusively employed with which, in addition to the reference electrode and the indicator electrode, an additional auxiliary electrode is immersed into the liquid to be analysed, and likewise connected to the electrical measuring device. By means of suitable electrical wiring, the potential between reference electrode and indicator electrode can, in the standard way, be controlled by means of the measuring device but, contrary to the two-electrode principle, with no current flowing through the reference electrode. Possible types of wiring for the electrodes can be derived from the relevant professional literature. The invention described in the following can be used independently of the measuring principle employed (two-or three-electrode principle).

A chemical reaction takes place at the indicator electrode during measurement. With that, the properties of the electrodes can change, and this will have a negative affect on the repeatability of the measurement. In order to obtain reliable measurement results, the indicator electrode must therefore be exchanged from time to time. In the case of polarography, a method of electroanalysis closely related to voltammetry, a dropping mercury electrode is used as an indicator. The mercury drop falls downwards at periodic intervals and is replaced by a new drop, so that the surface of the indicator electrode is continually renewed. Voltammetry employing solid electrodes has a few advantages with regard to polarography, however; the size of the indicator electrode is constant, and practically any type of material can be selected for for the indicator electrode.

As a rule, indicator electrodes with an electrode surface of at most 20 mm$^2$ are used. Particularly preferred are so-called microelectrodes, the electrode surface of which amounts to a maximum of 0,05 mm$^2$. These can employed both individually and in groups, a plurality of electrically connected microelectrodes being combined into an array of electrodes. These solid electrodes, made of one solid material, are also frequently exchanged, so that later measurements will not be influenced by a change to the indicator electrode (Memory Effect).

For a rational way of working during analysis it is therefore important that the indicator electrode can be easily replaced. FIG. 6 of WO-91/08474 shows a device for electroanalyis of liquids with which both indicator electrode and the larger reference electrode are attached to a common carrier plate. Both electrodes are connected via strip conductors to contact surfaces, and the contact surfaces are connected with an electrical measuring device by means of plugging of the carrier plate into an associated holder. In order now to replace the indicator electrode, the entire carrier plate must be removed from said holder and replaced by a new carrier plate. To this end, numerous manual steps are required, requiring the presence of an operator. Apart from that, the reference electrode is also replaced, which would otherwise not be necessary.

It is therefore a purpose of the invention to avoid the known disadvantages, and create a device for voltammetry which enables automatic replacement of the indicator electrode. With that, solely the indicator electrode, and not simultaneously also the reference electrode, should be replaced. According to the invention, this purpose is fulfilled by a device for voltammetry possessing the features of claim 1 and by a method for carrying out voltammetric analysis by means of such a device, according to the features of claim 19.

SUMMARY OF THE INVENTION

The device possesses a vessel for accommodation of a liquid to be analysed. A reference electrode is arranged in this vessel, beneath the anticipated liquid surface, said reference electrode being connected to a measuring device. If an analysis device is concerned which operates on the three-electrode principle, then an auxiliary electrode is provided in addition to the reference electrode, said auxiliary electrode likewise being connected to the electrical measuring device, and likewise being arranged beneath the anticipated surface of the liquid. Furthermore, a plurality of indicator electrodes are provided, of which at least one selected indicator electrode is located in the area of the vessel intended for the liquid. Furthermore, the device possesses an electrode changer, said electrode changer being coordinated with a sequence control, by means of which sequence control the selected indicator electrode can be replaced by one of the other indicator electrodes. This electrode changer enables automatic changing of the selected indicator electrodes. Such devices are, for example, suitable for voltammetric series examination, the replacement of the liquid to be analysed and the measurement procedure also being controlled by the control, in addition to changing of the indicator electrode. Apart from that, a means is anticipated for connecting the selected electrode to the electrical measuring device.

Within the meaning of the invention in question, every form of liquid container, into which liquid is continuually or intermittently introduced or aerated in constant flow or in batches, is to be conceived as a vessel. The invention, for example, can thus also be realised within an appropriately adapted tubular section which can function as a flow-through vessel.

A microelectrode is preferably employed as an indicator electrode. The effective electrode surface of a microelectrode amounts to at the most 0.05 mm$^2$. The effect of concentration polarisation, as exploited in voltammetry, is increased in an advantageous way by using indicator electrodes with smaller surfaces. Frequently, a plurality of microelectrodes arranged as an array are interconnected electrically and combined into one indicator electrode. Such microelectrodes can be manufactured with particular ease, in that an electrode material is covered with a dielectric layer of material. This cover possesses an opening, in the area of which the electrode material is exposed to become an effective electrode surface. In the case of an array of microelectrodes, a plurality of openings arranged as an array correspondingly provided in the dielectric layer of material. The entire electrode surface of the indicator electrode in this case corresponds to the total of all electrode surfaces combined into such an array. The number, size and arrangement of the microelectrodes of a microelectrode array will influence the accuracy and sensitivity attainable with the analysis, although this is not a part of the invention in question.

The necessary movement sequence required when changing the indicator electrode can be considerably simplified if an arrangement of indicator electrodes with a plurality of indicator electrodes is used, said arrangement being arranged on a common carrier. This common carrier is then mounted to move in relation to the vessel in such a way that at least one of the indicator electrodes is able to be selectively brought into the area of the vessel intended for the liquid, and into contact with the liquid. This will here be described as the "selected indicator electrode". Changing of the selected indicator electrode ensues by means of selecting a new electrode, said new electrode being located on the same carrier. In addition, the carrier is moved in relation to the vessel until a new electrode is located in the area intended for the liquid. Since all indicator electrodes are located on the same carrier, by means of simple movement of the carrier the feed of a new indicator electrode ensues simultaneously with the removal of the used indicator electrode. In order to carry out this movement automatically, the electrode changer possesses a movement drive which is coordinated with the carrier. Since, at each indicator electrode change, the same common carrier must be moved, said carrier can be connected with the movement drive in a simple way.

The effort required for manufacture of an indicator will also be less if a plurality of such electrodes are arranged on a common carrier. This is particularly the case if electrodes are used whose electrode material is covered by a dielectric layer of material in the way already described. The openings of this layer of material determine the effective electrode surface. If now a plurality of such electrodes are arranged on a common carrier, the possibility will thus arise for covering all indicator electrodes with a common dielectric layer of material. This will simplify production.

For automatic selection of an indicator electrode, or for automatic changing of a selected indicator electrode, the movement drive is connected with a sequence control. If the position of the indicator electrode on the carrier is sufficiently accurately known, positioning by control of the drive, for example using stepper motors, can ensue. Alternatively, it is also possible to ascertain the actual position of an indicator electrode using suitable sensors, and to activate the drive by means of the control for sufficient time until the indicator electrode concerned is in the area intended for the liquid. The actual design of the movement drive will depend on the design of the arrangement of indicator electrodes, and its arrangement in relation to the vessel. To this end there are various possibilities, of which the preferred are described in the following.

In the case of the first variant, the vessel possesses an opening in its upper area, through which opening the liquid to be analysed can be reached. For the analysis, a part of the arrangement of indicator electrodes is immersed into the liquid, indeed in such a way that only the selected indicator electrode comes into contact with said liquid. The carrier is preferably designed as a flexible carrier tape, on which the individual indicator electrodes are arranged, preferably lying consecutively in the longitudinal direction of the tape. tape form of carrier has the advantage that, wound onto a spool, it requires little space, also in the case of large tape lengths. Thus, arrangements of indicator electrodes with a plurality of indicator electrodes can be manufactured. A supply of electrode tape is wound onto a feed spool, and a means is provided for withdrawal of the carrier tape from the feed spool and selectively bringing one of the indicator electrodes into the area of the vessel intended for the liquid. A simple possiblility is the use of a take-up spool. The outer end of the carrier tape wound onto the feed spool is, with that, connected with the take-up spool in such a way that, through rotation of the take-up spool, said carrier tape can be wound off onto said take-up spool, onto and off the feed spool. With that, between both the spools the tape comes to partially lie in the area intended for the liquid, and through rotation of the take-up spool, the indicator electrodes are able to be brought sequentially into this area of the vessel. With this embodiment, the movement drive required for automation can be realised in a particularly simple way, namely with a rotational drive effective on the take-up spool.

Also in the case concerning the bringing of one of the indicator electrodes into the area of the vessel intended for the liquid, the flexible carrier tape has decisive advantages: this can be so guided in its longitudinal direction by suitable guide elements, for example deflection rollers, that one section of the tape runs in the area of the vessel intended for the liquid. By moving the tape in the longitudinal direction, the selected tape section can be so selected that at least one indicator electrode is located in the area intended for the liquid.

With an alternative embodiment, the area of the common carrier exposed to the liquid is more closely restricted to the selected indicator electrode. With that, the vessel possesses an opening beneath the anticipated level of the liquid. Furthermore, means are anticipated to bring the carrier, with selected indicator electrode, into liquid sealing engagement with the vessel opening. Both vessel opening and carrier are, advantageously, so designed that the carrier must undertake no complicated movement during changing of the electrode. This is achieved, for example, if the opening edge of the vessel opening lies approximately in the plane of said opening. The carrier is, with that, designed in such a way that it possesses one surface in which the indicator electrodes lie, and is so arranged that, in the area of the opening, said surface is aligned towards the opening, is parallel to the plane of the opening, and is able to be moved parallel to the plane of the opening for selection of an electrode. With that, not all of the indicator electrodes arranged on the carrier must lie in one plane. The surface with the indicator electrodes must be parallel to the plane of the opening solely in the area of the vessel opening. A carrier can be concerned, for example in the form of a flexible carrier tape which runs parallel to the vessel opening only in the area of the vessel opening.

The movement of the carrier parallel to the plane of the opening is in principle facilitated if said carrier does not make contact with the vessel opening. The vessel opening is thus preferably lifted away from the carrier during changing of the indicator electrode. This is made possible by means of a mounting which is vertically moveable in relation to the plane of the opening. As a result, in order to seal the opening, it is simultaneously possible, with indicator electrode selected, to press the vessel vertical to the plane of the opening against the carrier. To generate the pressing force, the weight of the vessel itself or a pretensioned spring, for example, can be used here. In order to improve the sealing properties, the vessel opening can be provided with an elastic sealing ring. The seal will also be improved if the carrier is of an elastic material, or if an elastic dielectric layer of material covers the carrier.

In order to bring the carrier, with indicator electrode selected, into sealed engagement with the vessel opening, a pressing element can be used. The pressing element has a flat pressing surface, said pressing surface being larger than the vessel opening and, in the area of this opening, being parallel to the plane of the opening. The carrier lies between the pressing surface and the vessel opening. With indicator electrode selected, said carrier can be brought into sealing engagement with the vessel opening by means of the pressing surface, said pressing surface serving as a form of abutment. For this purpose, for example the distance between the pressing surface and the plane of the opening can be changeable. Or at a constant distance, a pretensioned elastic seal can be used in order to seal the opening.

In combination with the vessel opening as described above, preferably carriers with a planar surface are used, on which surface the indicator electrodes are arranged. This surface is, with indicator electrode selected, brought into sealing engagement with the vessel opening. With that, the indicator electrodes are preferably so arranged on the carrier that said carrier must only be moved in one direction during electrode change. This will lead to a mechanically simple construction for the device. With that, a linear movement or a rotational movement can be concerned, the carrier being a disc and the indicator electrodes being arranged on a side surface of the disc. With that, the disc is displaceable within the plane of the disc, and in particular mounted to rotate. It is so arranged in relation to the vessel that its side surface possessing the electrode surfaces lies parallel to the plane of the vessel opening and is aligned towards said opening. Comparatively many indicator electrodes can be arranged within a small space on such a disc-shaped carrier. With this embodiment, preferably a linear or rotational drive coupled to the disc is used as a movement drive for automatic electrode change.

Also arrangements of indicator electrodes with a tape form carrier can be used in combination with the said vessel opening. The carrier tape has two wide surfaces, and the indicator electrodes are arranged on one of the two wide surfaces of the carrier tape. A supply of this carrier tape is wound onto a feed spool, and means are provided for withdrawal of the carrier tape from the feed spool, to selectively bring the electrode surface of one of the indicator electrodes into the area of the vessel opening. To this end, a take-up spool as previously described is preferably used.

If all indicator electrodes mounted on one carrier have been used up, the arrangement of indicator electrodes must be replaced. When mounting the carrier, it must therefore be taken into account that said carrier is easily changeable. To this end, easily replaceable interlocking and/or friction connecting elements, such as for example snap fasteners, are used. In the equipment manufacturing industry, a plurality of such connecting elements are state of the art and in use.

When using an arrangement of indicator electrodes in the form of a carrier tape, with a feed spool and a take-up spool as described above, the change of the electrode tape can be conceived in the most simple way if feed spool and take-up spool are mounted to rotate as part of a tape cassette within a cassette housing. If all the indicator electrodes on the tape are used up, said tape cassette can be removed as a whole, and replaced by a new cassette with new indicator electrodes. This embodiment has numerous essential advantages: the tape cassette is easily exchangeable as an independent unit. By means of the tape form design of the carrier, a very great number of indicator electrodes can be accommodated in a small space, wound onto a feed spool. With that, also in the case of frequent electrode change, fully automatic analysis operation is possible, with many hundreds of indicator electrodes being able to be used, for example during one night shift. Furthermore, changing of the selected indicator electrodes can be designed in a particularly simple way, since only one rotational drive is required for further transport of the indicator electrodes.

As in the case of the second reference electrode involved in the analysis, the selected indicator electrodes must be also connected to the electrical measuring device. To this end, an electrical contact element is preferably used. Each indicator electrode is allocated to an electrical contact element and electrically connected to said contact element. On the device, means are provided for connection of the contact element of the selected indicator electrode to the electrical measuring device. The type of this contact element as well as its connection with the electrical measuring device is primarily dependent on the construction of the arrangement of indicator electrodes. If said arrangement possesses solely a single contact element with which all indicator electrodes are connected, a reliable plug contact is preferably used in order to connect said contact element with the measuring device. With that, for example an arrangement of indicator electrodes can be concerned, the carrier of which is an electrical conductor serving as a common contact element for all microelectrodes. With that, a particularly simple construction of the arrangement of indicator electrodes will result.

In order to avoid influencing of the measurement results by conductors of varying lengths or by indicator electrodes which not involved in the measurement, arrangements of indicator electrodes can be used which possess the same number of electrical contact elements as indicator electrodes. With that, each contact element is exactly allocated to an indicator electrode and connected to said indicator electrode. In this case, at each electrode change, the contact element of the newly selected indicator electrode must be connected to the measuring device. For example, the contact element can be an electrically conducting surface, an electrical sensor being provided which senses the contact element of the selected indicator electrode and connects it electrically with the measuring device. The sensor can, particularly in the case of automatic electrode change, be brought into contact with the contact element of the newly selected indicator electrode more simply as would be the case, for example in the case of a plug connection.

The contact element allocated to a microelectrode must, on the multielectrode, be so arranged that, with indicator electrode selected, said contact element does not come into contact with the liquid to be analysed. The contact element is thus frequently arranged remote from the microelectrode. The electrical connection between electrode and contact element can, for example, be produced by means of a strip conductor lying between the carrier and the dielectric layer of material. The contact element can, with that, be integrally connected with the strip conductor and manufactured together with said strip conductor in a single working step. This can be easily integrated into the manufacturing process for microelectrodes, where the use of layer technology is standard. The strip conductor can, for example, can be manufactured by silk screen printing on the basis of thick-film technology.

In comparison to individual indicator electrodes, an arrangement of indicator electrodes with a plurality of indicator electrodes arranged on a common carrier can be produced considerably cheaper. For example, all indicator electrodes can possess a common dielectric layer of material. With one preferred production process, the basis is a plastic foil which serves as a dielectric layer of material. The thickness of the plastic foil is preferably between 10 μm and 100 μm; a material suitable for processing by means of photoablation is polyester. First of all, small perforations are created in this layer of material by means of photoablation, using a laser beam. With that, at least one such perforation is made for each indicator electrode; the area of the perforation will later form the electrode surface. For the manufacture of microelectrode arrays, a plurality of perforations is provided, said perforations being arranged in the form of an array with perforation diameters of preferably 20 μm to 40 μm, and a distance between perforations of preferably 100 μm and 300 μm. Alternatively, it is also possible, in place of round perforations, to use longitudinal slots or other shapes of perforations. Subsequently, an electrically conducting paste or liquid is applied to one side of the plastic foil. Preferably, a liquid is used which hardens after application, for example a liquid containing carbon or metal which is curable at low temperatures. This liquid serves as the electrode material, said electrode material being exposed as the electrode surface on the opposite side of the plastic foil in the area of the previously applied perforations. The size and number of the perforations per indicator electrode will determine the size of the electrode surface. Subsequently, the plastic foil coated with electrode material is applied to a carrier so that the electrode material comes to lie between said plastic foil and said carrier. As a rule, dielectric material will likewise be used as a carrier. In the case of a tape carrier, care must be taken that the tape remains flexible so that it can be wound onto a spool. A plastic film is here preferably used as a carrier, the thickness of which lies between 0,1 mm and 1 mm. To this end, any mechanical flexible plastic can be used, for example polyester. The electrode material can at the same time serve as a strip conductor, in order to connect the indicator electrodes with a contact element. With that, for example an electrically conducting layer arranged on the carrier, can be concerned. Alternatively, the electrode material itself can be used as contact element.

Due to fully automated indicator electrode changing, the device described for voltammetry is particularly suitable for carrying out voltammetric series examinations. In this case a plurality of liquids are analysed concsecutively, in each case the analysed liquid being removed from the vessel after completion of a measurement and replaced by a fresh liquid to be analysed. Both the replacement of this liquid, and the change of indicator electrodes, is carried out automatically, and is controlled by a sequence control. The change of indcator electrodes ensues according to predeterminable sequences, such as, for example, attainment of a maximum operating time for an indicator electrode, or attainment of a maximum number of measurements which should be carried out using the same indicator electrode. Preferably, a sequence control is used with an input device, on which the necessary parameters for determining the point in time for an electrode change can be entered.

The contact between the liquid to be examined and the small electrode surface will be improved if the surface of the dielectric layer of material, at least in the area bordering the electrode surface, is roughened. As a result, said surface will become more hydrophilic. This roughening can preferably be achieved by means of a laser beam, by which means the openings for the electrode surface are also created.

BRIEF DESCRIPTION OF THE DRAWINGS

The invention is more closely explained in the following, with the aid of the drawings. Namely:

FIG. 1A schematic representation of a fully automated voltammetry device,

DESCRIPTION OF THE PREFERRED EMBODIMENT

Figure 1:
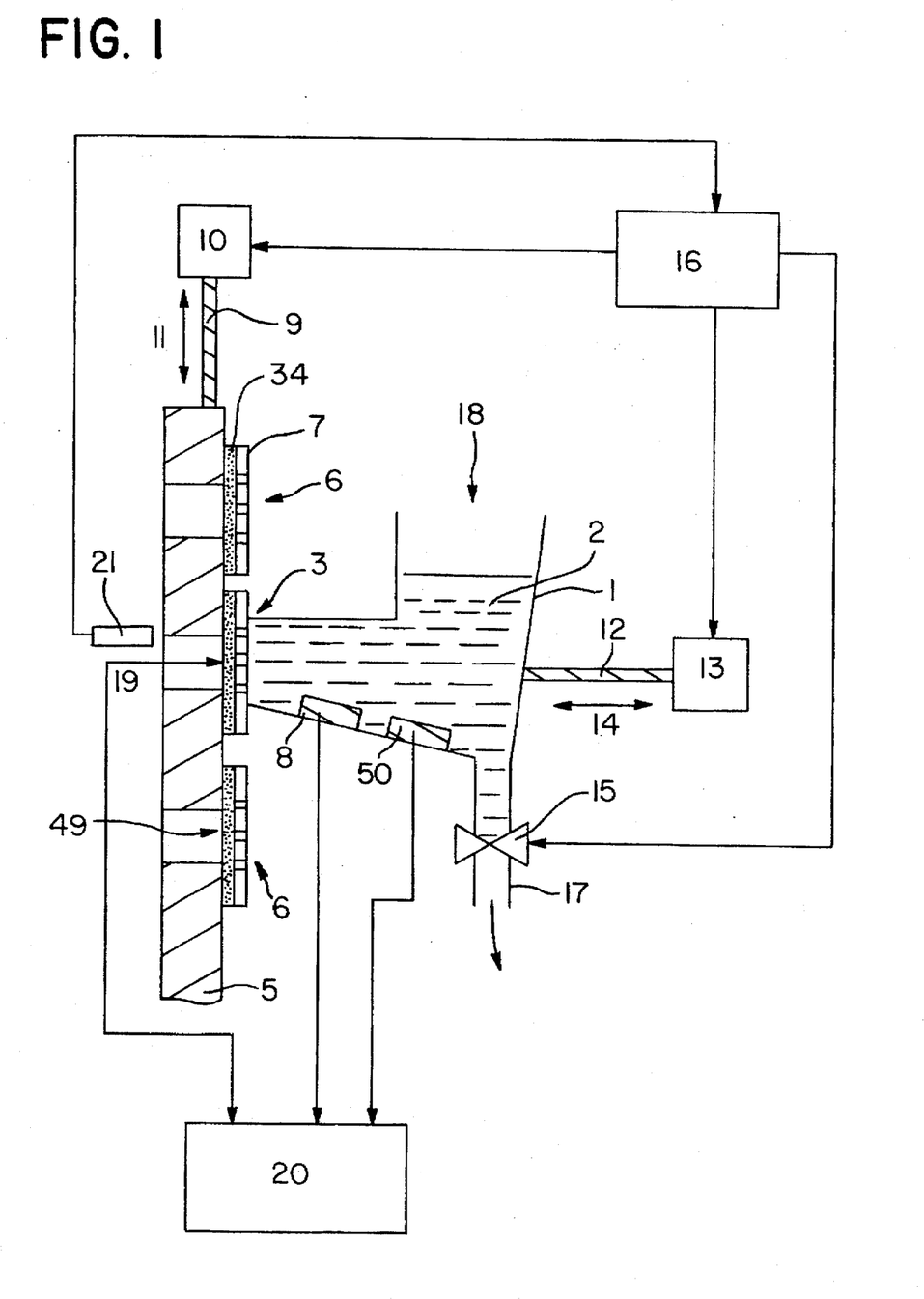

In FIG. 1, a device for fully automated voltammetry is schematically represented. It possess a vessel 1 for accommodating the liquid 2 to be analysed. This vessel has, in its area intended for the liquid, an opening, the opening edge 3 of which lies approximately in one plane. An arrangement of indicator electrodes is provided outside of the vessel 1. Said arrangement of indicator electrodes comprises a carrier 5 on which a plurality of indicator electrodes 6 are arranged, said indicator electrodes comprising an electrode material 34 covered by a dielectric layer of material 7. The carrier is mounted to move in the axial direction 11. Through movement of the arrangement of indicator electrodes in this direction, any indicator electrode arranged on the carrier can be brought into the area of the vessel opening. This procedure is also known as "selecting". The selected indicator electrode is located in the area of the vessel opening, and thus in the area of the vessel intended for the liquid. If a liquid to be analysed is introduced into the vessel, said liquid will come into contact with the selected indicator electrode. The arrangement of indicator electrodes is so designed and arranged that, with indicator electrode selected, it can be brought into liquid sealing contact with the vessel opening. For this purpose, the vessel is mounted to move in the axial direction 14, vertical to the plane of the opening. With indicator electrode selected, it can thus be pressed against the arrangement of indicator electrodes in order to seal the vessel opening. During change of the indicator electrode, said vessel is moved in the opposite direction and lifted away from the carrier, so that said carrier is free to move in the axial direction 11.

The figure shows the device with indicator electrode selected and with the liquid 2 to be analysed already introduced. For measurement according to the three-electrode principle, a reference electrode 8 and an auxiliary electrode 50 are additionally required, and these are arranged within the vessel 1. Said reference and auxiliary electrodes, as also the indicator electrode, are connected to the measuring device 20. In addition, the indicator electrode is connected to a contact element, said contact element being sensed by an electrical sensor 19 and thus connected with the measuring device. With this example, the electrode material 34 exposed on the rear side of the indicator electrode at the same time serves as a contact element 49. The carrier 5 possesses an opening in the area of the indicator electrode so that the contact element 49 can be reached by the sensor 19.

After completion of the measurement, the vessel 1 is emptied. Subsequently, a fresh liquid to be examined can be filled, and a new measurement can commence. A suction pipe 17 is provided in order to empty the vessel; filling of a fresh liquid ensues through the filler opening 18. The indicator electrode must not necessarily be changed after every measurement. Changing will depend on the measuring accuracy required, and the liquid to be examined.

A particular advantage of indicator electrodes arranged on a common carrier is the simple possibility for complete automation of the analysis. A plurality of liquids can thus, without the presence of an operator, be fully automatically analysed, for example during the night. Changing of the indicator electrode is in this case of considerable importance. The carrier is, for this purpose, connected via an operating linkage 9 to a movement drive 10 which permits the automatic movement of the carrier in the axial direction 11. Furthermore, the vessel 1 is connected via an operating linkage 12 to a movement drive 13 which permits movement of the vessel in the axial direction 14, and thus pressing or lifting away of the vessel opening from the carrier. The automatic analysis is controlled by a control 16, said control being coordinated with the movement drives 10 and 13. Furthermore, said control is also connected with a valve 15 in the suction pipe 17, so that emptying of the vessel 1 can ensue, controlled be the control 16. If the indicator electrode is to be changed after a measurement, the following sequence will ensue: first of all the control 16 will activate the valve 15, and the liquid located in the vessel will be sucked away through the suction pipe 17. Subsequently, the movement drive 10 will be activated by the controller 16, and the vessel will be lifted away from the carrier, vertically to the plane of the opening. In the next step, the movement drive 10 will be activated by means of the control 16, so that the carrier moves in the axial direction 11. This movement will be carried out for sufficiently long until a new indicator electrode is located in the area of the vessel opening. In addition, a position sensor 21 is provided, said position sensor transmitting a signal to the control 16 as soon as an indicator electrode is located in the area of the vessel opening. Such a position sensor can also be dispensed with, as long as the position of the electrodes on the carrer is exactly known. In this case, positioning can ensue purely by means of positional control of the drive 10, for example by means of stepper motors. When the new indicator electrode is in position, the movement drive 13 is once again activated, this time in the opposite direction, so that the vessel is pressed against the arrangement of indicator electrodes in the axial direction 14, vertically to the plane of the opening, and will form a seal with said arrangement of indicator electrodes. Subsequently, fresh liquid to be examined can be filled through the filler opening 18. This, too, ensues automatically through a pipette device controlled by the control 16, and not shown here.

Figure 2:
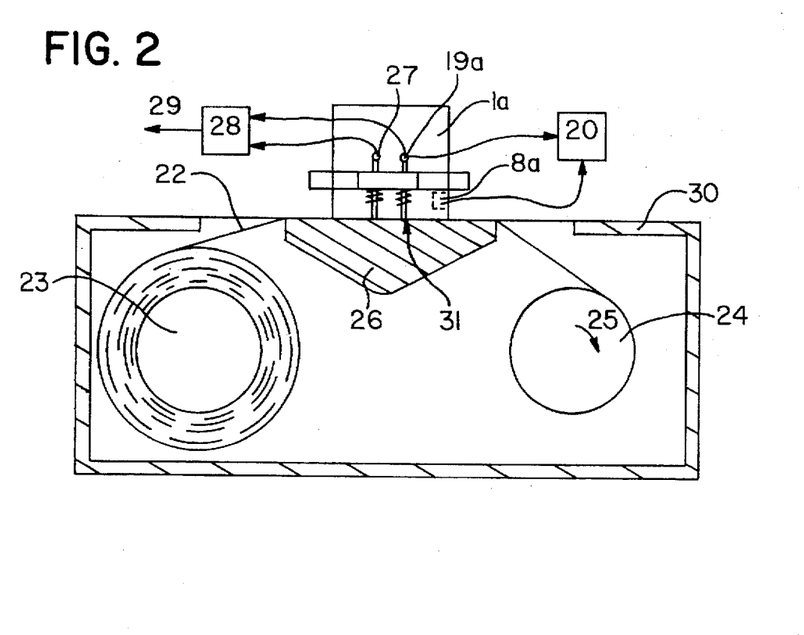
FIG. 2 a schematic representation of a voltammetry device with a carrier tape integrated into a tape cassette, FIG. 3 a schematic representation of a detail of the device according to FIG. 2, FIG. 4 a schematic detail of a carrier tape, FIG. 5 a schematic detail of an alternative carrier tape, FIG. 6 a schematic representation of a voltammetry device with a carrier tape integrated into a tape cassette, FIG. 7 a schematic representation of a voltammetry device with immersed carrier tape, and FIG. 8 a schematic representation of an alternative embodiment of a voltammetry device with an indicator electrode changer.

The voltammetry device shown in FIG. 2 possesses a vessel 1a in the form of a cylindrical tubular section, said vessel standing upon an tape form arrangement of indicator electrodes. The carrier tape, together with the vessel standing upon it, is more clearly shown in FIG. 3. Both ends of the tubular vessel 1a are open. In relation to its axial direction, the vessel stands vertically on the carrier tape, the upper opening being the filler opening and the lower opening being able to be brought into sealing contact with the carrier tape. The indicator electrodes, which are arranged on the carrier tape 22 in the longitudinal direction of the tape, cannot be seen in FIG. 2.

Figure 3:
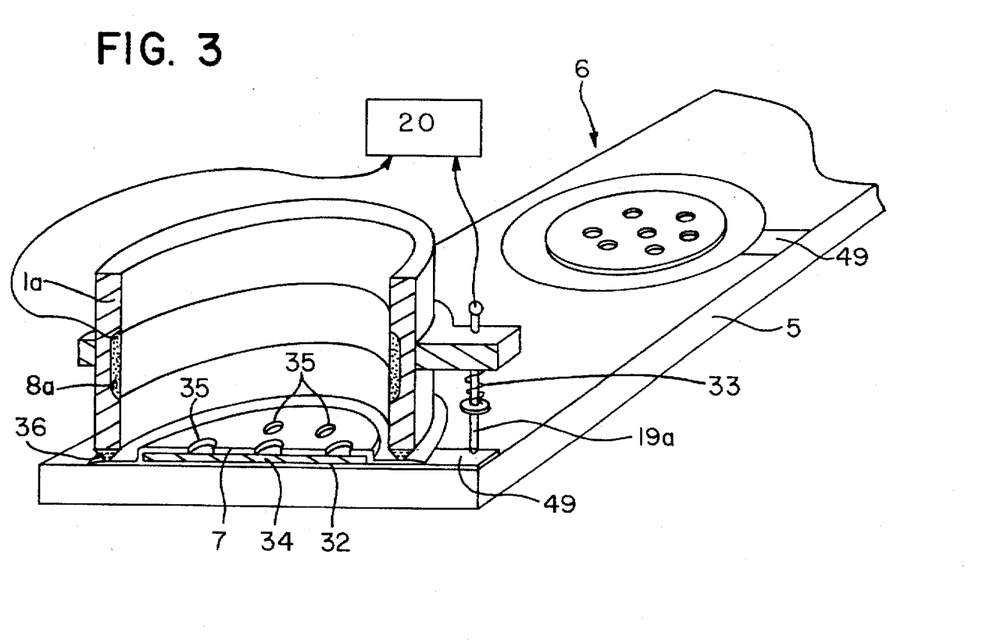

The three dimensional representation according to FIG. 3, which shows a detail of the device shown in FIG. 2, is likewise a schematic representation. In particular, the relative proportions of the individual elements are not reproduced true to scale. For example, the electrode surfaces 35 of the indicator electrodes comprising an array of microelectrodes are considerably smaller in comparison to the vessel 1a, and the reference electrode 8a contained therein. On the tape detail shown, two indicator electrodes can be seen, of which one is portrayed as a section, as is the vessel 1a arranged upon it.

The indicator electrodes shown here comprise electrically conducting material 34 which, for example, is applied by means of silk screen printing onto the carrier 5 and subsequently covered by a dielectric layer of material 7. With that, preferably a polymer film is concerned which, for example, is applied by vapour polymerisation. Furthermore, a strip conductor 32 is allocated to the indicator electrode. Said strip conductor is located on the carrier 5, and extends beneath the electrode material 34. Its outer exposed end serves as a contact element 49 which can be sensed outside the vessel 1a by a sensor pin 19a in order to connect the electrode material 34 electrically with the measuring device 20. The sensing pin 19a, which is mounted to displace axially in the holder 47, is loaded by a spring 33 with a spring force, and is pressed against the contact element 49 by this spring 33. In the area of the vessel opening, the strip conductor 32 runs between the dielectric layer of material 7 and the carrier 5, and is therefore not exposed to the liquid to be examined.

The dielectric layer of material possess a plurality of perforations, in the area of which the electrically conductive material 34 is exposed as the electrode surface. The reference electrode 8a is affixed to the inner wall of the vessel 1a, and likewise connected to the measuring device 20 by means of an electrical connection. In order to analyse a liquid, said liquid must be introduced into the vessel in sufficient quantity so that, in addition to the indicator electrode also the reference electrode 8a comes into contact with the liquid. After completion of analysis, emptying of the vessel can ensue in various ways, most simply through lifting of the vessel 1a or, similarly, through lowering of the carrier tape. With that, the vessel opening is disengaged from the carrier tape and the liquid can flow out. Alternatively, the liquid can also be sucked out by a suction device which is not shown here and which, for example, can be introduced into the vessel through the upper vessel opening. Such suction devices have been in use in automatic chemical analysis equipment for some considerable time.

In order to change the indicator electrodes, with this example it is necessary to lift the vessel opening away from the carrier tape. The vessel 1a is for this purpose mounted to displace vertically on a holder which is not shown here. As an alternative, it would also be possible to hold the vessel still, and lower the carrier tape accordingly. Said carrier tape is subsequently moved in the longitudinal direction of the tape, parallel to the plane of the opening, until ,a new indicator electrode is located in the area of the vessel opening.

As can be seen in FIG. 2, a feed spool 23 is provided, on which a supply of the feed tape 22 is wound. Furthermore, a take-up spool 24 is provided, and the outer end of the carrier tape wound onto the feed spool is connected with the take-up spool 24 in such a way that, through rotation of said take-up spool in the direction of rotation 25, said tape can be wound off onto said take-up spool, onto and off the feed spool. Between both the spools, the carrier tape runs over a guide element 26. This guide element 26 simultaneously fulfills the function of a pressing element. It possesses a pressing surface 31 which is parallel to the plane of the opening in the area of the vessel opening. This serves as a form of abutment for the carrier tape if the vessel is pressed against the carrier tape 22 in order to seal the opening. In the area of the vessel opening, the carrier tape 22 runs, guided by the guide element 26, parallel to the plane of the opening. Movement of the carrier tape in order to select an indicator electrode ensues through rotation of the take-up spool in the direction of rotation 25. For automation of the electrode change, a rotational drive is used which takes effect on the take-up spool 24, said take-up spool corresponding in its function to the movement drive 10 as shown in FIG. 1. A second electrical sensor 27 is provided in addition to the electrical sensor 19a, in order to detect the positioning of an indicator electrode in the area of the vessel opening. The strip conductor shown in FIG. 3 is sufficiently wide that both the sensor pins 19a and 27 make contact with the strip conductor 32 at the same time when the indicator electrode is located in the area of the vessel opening. Both the sensor pins are connected to a position detector 28 which detects this occurrence for example by means of a resistance measurement, and creates a position signal 29 from said resistance measurement. This corresponds to the position sensor 21 shown in FIG. 1; the position signal 29 is connected to a control not shown in FIG. 2, said control being responsible for the coordination of the electrode change.

The feed spool 23 and the take-up spool 24 are mounted to rotate as components of a tape cassette in a cassette housing 30. In the area of the guide element 26, the carrier tape is accessible from outside of the cassette housing; this is the working area of the tape cassette. In this example, the tape 22 runs in the working area of the tape, outside the cassette housing 30.

Figure 4:
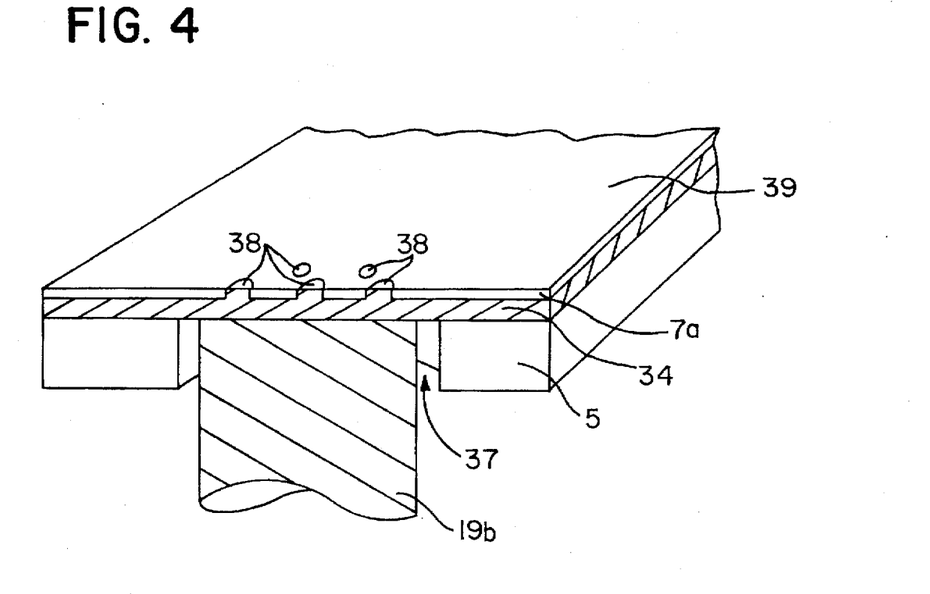

FIG. 4 shows a schematic detail of a tape form arrangement of indicator electrodes. As opposed to the embodiment shown in FIG. 3, the carrier tape possesses a flat outside surface 39 within which the electrode surfaces 38 lie. With this type of arrangement of indicator electrodes, lifting up of the vessel opening during electrode change can be dispensed with. Displacement of the carrier tape is possible, also if said carrier tape remains in engagement with the vessel opening. A further advantage of this form of electrode is its simple manufacture. All indicator electrodes, of which naturally only one is shown, are covered by a common dielectric layer of material 7 which extends over the entire length of the tape. By this means, the laborious polymerisation of the dielectric layer is dispensed with, and a continuous plastic tape can be used. With the manufacture of this arrangement of indicator electrodes, first of all small perforations are made in a thin strip of dielectric material. Preferably, a plastic tape is used and the perforations are created by a laser beam by means of photoablation. In a second step, electrically conducting material 34 is applied on one side of the dielectric layer of material. With that, in the area of the perforations, said electrically conducting material is pressed into the perforations so that it becomes exposed as the electrode surface 39 on the other side of the dielectric layer of material 7. The number, spacing and size of the microperforations will define the character of the indicator electrode. Preferably, a liquid containing metal or carbon is used as the electrode material, said liquid being curable at low temperatures of preferably 60°–80° C., after application. This tape is subsequently joined to a thicker carrier tape 5, so that the layer 34 of electrically conducting material comes to lie between the dielectric layer of material 7a and the carrier 5. With this example, the carrier 5 possesses a recess 37 in the area of the indicator electrode, so that the electrode material 34 is exposed in the area of this recess and can be simultaneously used as a contact element. In order to electrically connect the indicator electrode with the measuring device, an electrical sensor 19b is provided, said sensor protruding into the recess 37 and making contact with the conducting material serving as a contact element.

Figure 5:
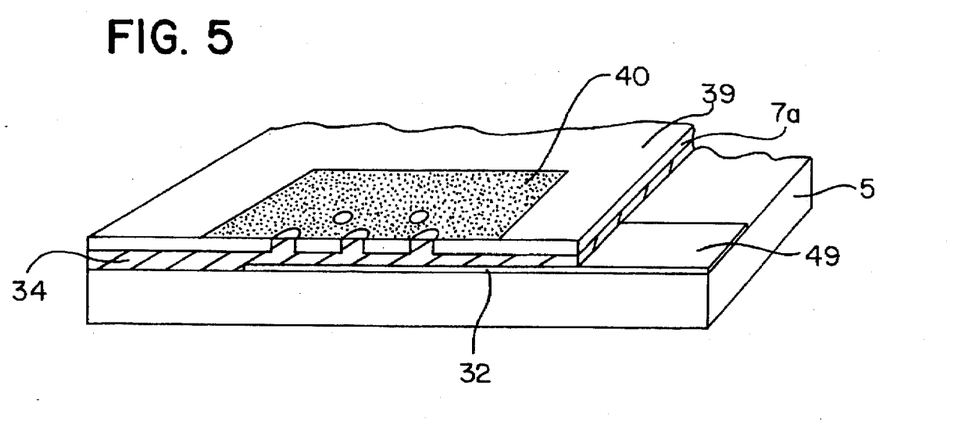

FIG. 5 shows a modified embodiment of the arrangement of indicator electrodes according to FIG. 4. The carrier 5 is here wider than the dielectric layer of material 7a. A strip conductor 32 is arranged on the carrier tape 5. This tape form arrangement of indicator electrodes could be used together with the vessel as shown in FIG. 3 or a device according to FIG. 2. The outside surface 39 of the dielectric layer of material 7a is roughened in the area bordering on the electrode surface, so that the surface is hydrophilic. The construction otherwise corresponds to that described in FIG. 4.

Figure 6:
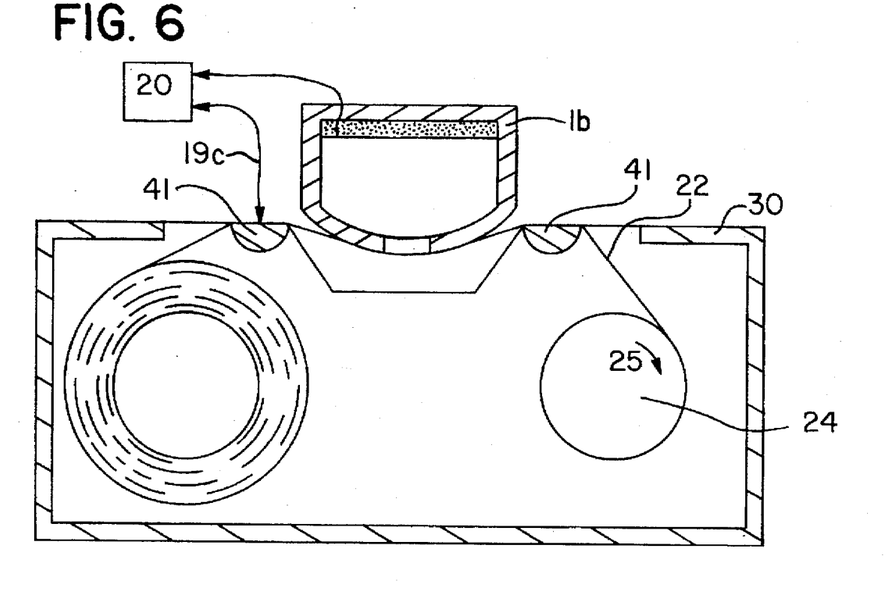
Figure 7:
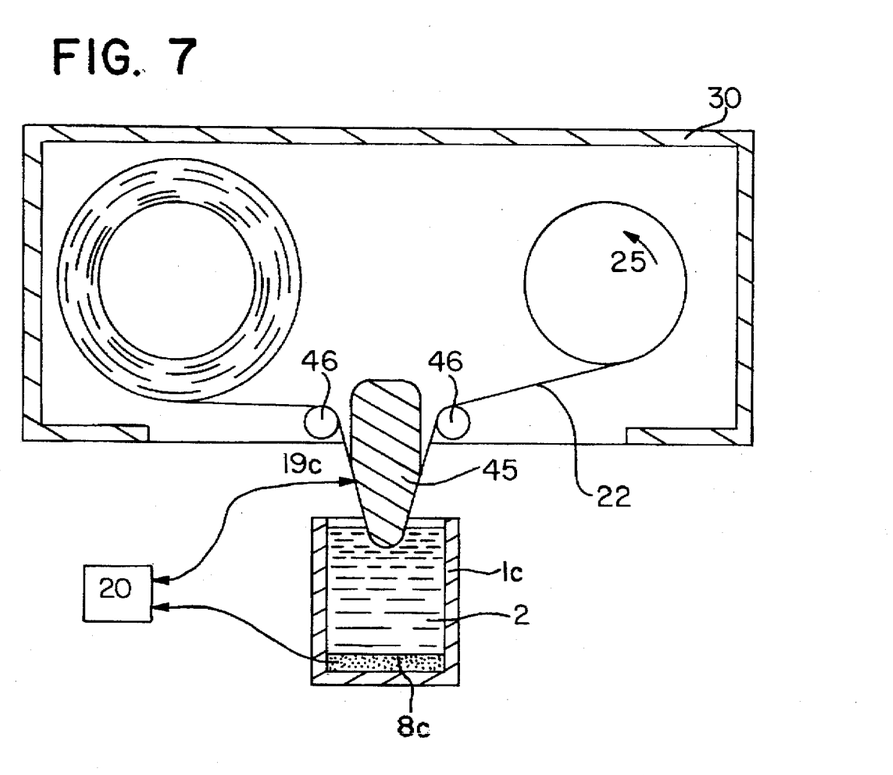

FIGS. 6 and 7 show alternative embodiments for the guidance of the carrier tape 22. This is here similar to that described in FIG. 2, with two connected spools mounted in a tape cassette 30.

The variant shown in FIG. 6 corresponds to that of FIG. 2 to a large extent. However, it possesses no pressing element to press the carrier tape 22 against the vessel opening. The carrier tape 22 is guided by two guide elements 41 in such a way that it comes to lie against the vessel 1b in the area of the vessel opening, and is pulled against the vessel opening through tensioning of the carrier tape. The side wall 43 of the cassette housing 30 possesses a recess 44 so that a free space will occur between the guide elements 41, said free space intended for the vessel 1b. With this embodiment, a tape form of arrangement of electrodes with a smooth outer surface is preferably used, as shown in FIGS. 4 and 5. Electrode changing is in this case further simplified since, in order to bring said opening into engagement with the tape, no movement of the vessel or the tape cassette is required vertical to the plane of the opening. Engagement ensues through simple tensioning of the tape, which for example is possible by means of a torque control on the rotational drive, effective on the take-up spool 24. The symbolic sensor pin 19c is arranged above one of the guide elements 41. The contact element allocated to the selected indicator electrode is located in the area of the sensor pin 19c, and is sensed by said sensor pin. In the case of the carrier tape used here, the contact element is thus, in the longitudinal direction of the tape, remote from the indicator electrode allocated to it. The sensor pin 19c is, as also the reference electrode 8b within the vessel 1b, electrically connected to the measuring device 20.

In order to selectively bring one of the indicator electrodes into contact with the liquid to be examined, the variation according to FIG. 7 uses a principle which deviates from the embodiments discussed up until now. The vessel 1c is open at its upper end and the carrier tape 22 is guided through the guide elements 45, 46 in such a way that a short tape section is immersed into the liquid 2 to be analysed. The selected electrode, which is not show here, is located at the lowest point 48 of the carrier tape. The contact element allocated to the indicator electrode is arranged to be displaced in the longitudinal direction of the tape in relation to said indicator electrode; it is located beneath the electrical sensor 19d and is sensed by said sensor. This sensor, together with the reference electrode 8c arranged on the floor of the vessel 1c, is connected to the measuring device 20. The devices necessary for sucking out the liquid and for filling of fresh liquid are not shown. The same applies to FIG. 6.

Figure 8:
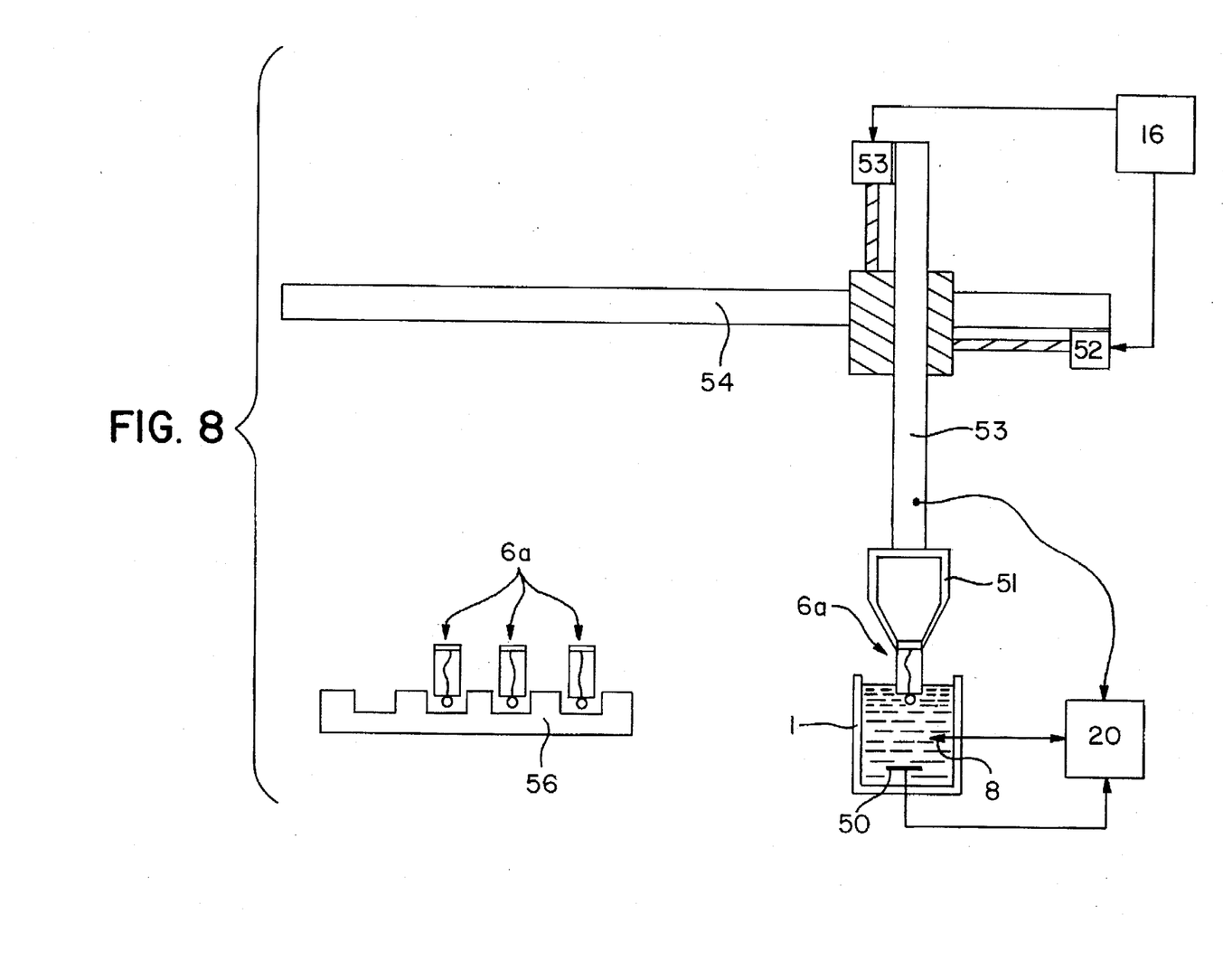

FIG. 8 shows a schematic representation of an alternative voltammetry device with an indicator electrode changer. The indicator electrodes 6a used with this device can be moved independently from one another. The electrode changer comprises a grabbing arm 51, said grabbing arm being mounted to move in horizontal and vertical directions on linear guides 53, 54. Apart from that, the grabbing arm 51 is coupled to a horizontal drive 52 and a vertical drive 53. These drives permit movement of the grabbing arm 51 in one plane and are controlled by the control 16. A supply of indicator electrodes is accommodated in an electrode magazine 56 within reach of the grabbing arm, and one of these electrodes can be brought into the area of the vessel intended for the liquid to be analysed with said grabbing arm 51. The grabbing arm 51 holds the indicator electrode during the analysis, and simultaneously connects said indicator electrode to the measuring device 20. The reference electrode 8 and the auxiliary electrode 50 are also connected electrically to the measuring device.

Inasmuch as the invention is subject to modifications and variations, the foregoing description and accompanying drawings should not be regarded as limiting the invention, which is defined by the following claims and various combinations thereof.

I claim:

1. Device for voltammetry comprising a vessel (1) with and area intended for accommodation of a liquid (2) to be analyzed, a reference electrode (8) arranged in said vessel in the area intended for the liquid, a measuring device (20) connected to the electrode, a carrier for mounting a plurality of indicator electrodes (6) and for bringing at least one selected indicator electrode into the area of the vessel (1) intended for the liquid in order to contact the liquid.

a movement drive coupled to a sequence controller for controlling movement of the carrier and means (19) for connecting the selected indicator electrode in the area of the vessel intended for the liquid with the electrical measuring device (20).

2. Device according to claim 1 wherein the area of the vessel intended for the liquid, an auxiliary electrode (50) is provided in addition to the selected indicator electrode (6) and the reference electrode (8), said auxiliary electrode being likewise connected with the electrical measuring device.

3. Device according to claim 8 wherein the indicator electrodes are arranged on a common carrier (5) and said carrier is mounted to move in relation to the vessel (1) in such a way that at least one of the indicator electrodes is able to be selectively brought into the area of the vessel intended for the liquid and into contact with the liquid.

4. Device according to claim 3 wherein the vessel (1) has an opening (3) in the area intended for the liquid and wherein the carrier (5) is movable so as to bring a selection of indicator electrodes (6) into sealing engagement with the vessel opening.

5. Device according to claim 3 wherein the carrier is a carrier disc and the indicator electrodes are arranged on a side surface of the carrier disc, and the carrier disc is rotatable about its axis.

6. Device according to claim 3 wherein the carrier comprises an electrically conducting material and serves as a common contact element for all the indicator electrodes.

7. Device according to claim 3 wherein the carrier (5) possesses at least one contact element (49) and each indicator electrode (6) is allocated to a contact element and is electrically connected with said contact element by means of a strip conductor (32) lying between the layer of dielectric layer of material and the carrier.

8. Device according to claim 3 wherein the carrier is a flexible carrier tape (22) on which the indicator electrodes are arranged.

9. Device according to claim 8 wherein a carrier tape (22) is wound onto a feed spool (23), a free end winding is connected with a take-up spool (24) in such a way that the carrier tape is able to be wound off the feed spool, the tape passing through the area of the vessel intended for the liquid, and wherein the indicator electrodes are sequentially brought into this area of the vessel through rotation of the take-up spool.

10. Device according to claim 9, further comprising a tape cassette housing, wherein the feed spool (23) and the take-up spool (24) are mounted to rotate, as part of a tape cassette, within said housing (30).

11. Device according to claim 1 wherein each indicator electrode comprises a core covered with a layer of dielectric material (7), said layer of dielectric material having at least one opening (35) in the area of which opening the electrode material is exposed as an effective electrode surface.

12. Device according to claim 11 wherein the electrode material (34) of all the indicator electrodes arranged on the carrier is covered by a common dielectric layer of material (7a).

13. Device according to claim 11 wherein the indicator electrode is formed as a microelectrode or a plurality of microelectrodes arranged in the form of an array (38), the effective surface of each electrode being not more than 0.05 $mm^2$.

14. Device according to claim 11 wherein the surface of the dielectric layer of material (39) is roughened at least in the area bordering on the electrode surface so that the surface is hydrophilic.

15. Arrangement of indicator electrodes designed and adapted as indicator electrodes for a device for voltammetry comprising a vessel with an area intended for accommodating a liquid to be analyzed, a reference electrode arranged in the area intended for the liquid, a measuring device connected to the electrode, a carrier for a plurality of said indicator electrodes, outside of the vessel and for bringing at least on selected indicator electrode into the area of the vessel intended for the liquid in order to contact the liquid, a movement drive coupled to a sequence controller for controlling the movement of the carrier and means for connecting the selected indicator electrode in the area of the vessel intended for the liquid with the electrical measuring device.

16. Tape cassette for a device comprising a cassette housing containing a feed spool (23) and a take-up spool (24), a supply of carrier tape with a plurality of electrodes wound onto the feed spool (23) and the end of this supply winding being connected to the take-up spool so that the tape, through rotation of the take-up spool, can be wound off the feed spool, the carrier tape being desired and adapted as a carrier for a device for voltammetry comprising a vessel (1) with an area intended for accommodating a liquid (2) to be analyzed, a reference electrode (8) arranged in said vessel in the area intended for the liquid, a measuring device (20) connected to the electrode, said carrier being adapted for mounting a plurality of indicator electrodes (6) outside of the vessel and for bringing at least one said selected indicator electrode into the area of the vessel (1) intended for the liquid in order to contact the liquid, and a movement drive coupled to a sequence controller for controlling the movement of the carrier and means for connecting the movement of the carrier and means for connecting the selected indicator electrode in the area of the vessel intended for the liquid with the electrical measuring device.

17. Method of carrying out a voltammetric analysis comprising steps of selecting at least one indicator electrode from a plurality of indicator electrodes (6, 6a) mounted on a carrier, bringing said selected electrode into the area of the vessel intended for accommodating a liquid to be analyzed by moving said carrier with a movement drive, and automatically replacing said selected indicator electrode with a subsequent indicator electrode arranged on said carrier according to a predetermined sequence, wherein the indicator electrode in the area is connected to an electrical measuring device (20).

\* \* \* \* \*